(12) United States Patent
Wilmes et al.

(10) Patent No.: US 6,447,728 B1
(45) Date of Patent: Sep. 10, 2002

(54) EXCHANGEABLE OSCILLATING PIPETTE NEEDLE

(75) Inventors: Hugo Wilmes, Bad Soden; Oliver Kube, Frankfurt, both of (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 09/418,585

(22) Filed: Oct. 15, 1999

(30) Foreign Application Priority Data

Oct. 16, 1998  (DE) .......................................... 198 47 759

(51) Int. Cl.⁷ .......................... B01L 3/02; G01N 21/00; G01N 1/10; B32B 27/04
(52) U.S. Cl. .......................... 422/100; 422/64; 422/65; 422/66; 422/67; 422/102; 73/864; 73/864.01; 73/864.11; 73/863.32; 436/180
(58) Field of Search .......................... 422/100, 64, 65, 422/66, 67, 102; 73/864, 864.01, 864.11, 863.32; 436/180

(56) References Cited

U.S. PATENT DOCUMENTS

| | | | | |
|---|---|---|---|---|
| 3,492,876 A | * | 2/1970 | Bull et al. | |
| 3,763,705 A | * | 10/1973 | Strande | |
| 4,204,515 A | * | 5/1980 | Seifert et al. | 125/16 R |
| 4,325,909 A | * | 4/1982 | Coulter et al. | |
| 4,462,097 A | * | 7/1984 | Janda et al. | 369/248 |
| 4,726,238 A | * | 2/1988 | Reese et al. | |
| 4,758,125 A | * | 7/1988 | Wahl | 412/39 |
| 5,084,242 A | * | 1/1992 | Sakuma et al. | 422/100 |
| 5,164,318 A | * | 11/1992 | Sato et al. | 435/288 |
| 5,264,182 A | * | 11/1993 | Sakagami | |
| 5,334,349 A | * | 8/1994 | Kellin et al. | |
| 5,398,652 A | * | 3/1995 | Jackson | 123/197.4 |
| 5,474,744 A | * | 12/1995 | Lerch | 422/100 |
| 5,493,384 A | * | 2/1996 | Matsuno et al. | 355/326 R |
| 5,501,948 A | * | 3/1996 | Hofstetter et al. | 436/518 |
| 5,705,815 A | * | 1/1998 | Heesch | 250/341.2 |
| 5,789,252 A | * | 8/1998 | Fujita et al. | 436/49 |
| 5,807,523 A | * | 9/1998 | Watts et al. | 422/64 |
| 5,814,277 A | * | 9/1998 | Bell et al. | 422/67 |
| 5,879,944 A | * | 3/1999 | Komatsu | 436/50 |
| 5,895,630 A | * | 4/1999 | Skaborn et al. | 422/100 |
| 6,197,255 B1 | * | 3/2001 | Miyake et al. | 422/64 |
| 6,270,726 B1 | * | 8/2001 | Tyberg et al. | |

* cited by examiner

Primary Examiner—Jill Warden
Assistant Examiner—Brian R. Gordon
(74) Attorney, Agent, or Firm—Finnegan, Henderson, Farabow, Garrett and Dunner, L.L.P.

(57) ABSTRACT

An exchangeable oscillating pipette needle for an automatic analyzer for examining biological body fluids is provided, in which the analyzer has a holder provided with a tension spring, and with which the oscillating arm, carrying the pipette needle and resting on a knife-edge bearing, is fixed in a stationary position and is releasably connected.

13 Claims, 4 Drawing Sheets

EXCHANGEABLE OSCILLATING PIPETTE NEEDLE

BACKGROUND OF THE INVENTION

1. Field of the Invention

The invention relates to an exchangeable oscillating pipette needle for an automatic analyzer for examining biological body fluids.

2. Description of the Related Art

It is known that in automatic analyzers which are used for examining biological body fluids, the required reagents are introduced into a measurement cell by means of an oscillating pipette needle. The pipette needle also has the role of ensuring that the body fluid to be examined is thoroughly mixed with the reagents. For this purpose, it is necessary for the pipette needle to be moved in oscillations. When introducing the reagents, and during the subsequent oscillations, there is a risk of the sensitive pipette needle colliding with the measurement cell or other apparatus parts, being damaged as a result, and having to be replaced because it is no longer fit for use. To date, exchanging the pipette needle has been associated with considerable technical effort, which can only be provided by a suitably trained service engineer. Not only do the pipette needle and other mechanical parts need to be exchanged, but also the motor and the means of heating the pipette needle. The associated lost time and the costs involved led to the need to develop a new construction for an oscillating pipette needle which allows the personnel operating the analyzer to exchange a damaged pipette needle quickly and in a straightforward way without having to call on the services of a specially trained engineer.

SUMMARY OF THE INVENTION

It is the object of the present invention to provide an oscillating pipette needle which is easily replaceable. This object is fulfilled by the present invention, an oscillating pipette needle for an automatic analyzer for examining biological body fluids, in which, for the purpose of introducing the pipette needle into the analyzer and withdrawing it from the analyzer, a holder 1 is provided which is equipped with a tension spring 3 and with which the oscillating arm, carrying the pipette needle 4 and resting on a knife-edge bearing, is fixed in a stationary position and is releasably connected.

BRIEF DESCRIPTION OF THE DRAWINGS

The construction of the exchangeable oscillating pipette needle according to the invention is illustrated by appended FIGS. 1 through 6.

DETAILED DESCRIPTION OF THE PREFERRED EMBODIMENT

Figure 1:
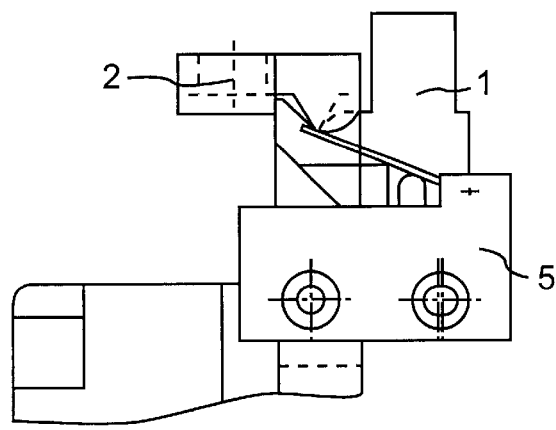
FIG. 1 is a right side view of the mutual engagement of holder 1 and oscillating arm 2 according to the present invention.

FIG. 1 shows in detail that the oscillating arm 2 bearing on a holder 1 is in contact with a sensor 5. If the pipette needle 4 secured on the oscillating arm 2 strikes against a solid object, then the oscillating arm 2 lifts and the flow of electrical current is interrupted by the sensor 5 secured on a plate 10.

Figure 2:
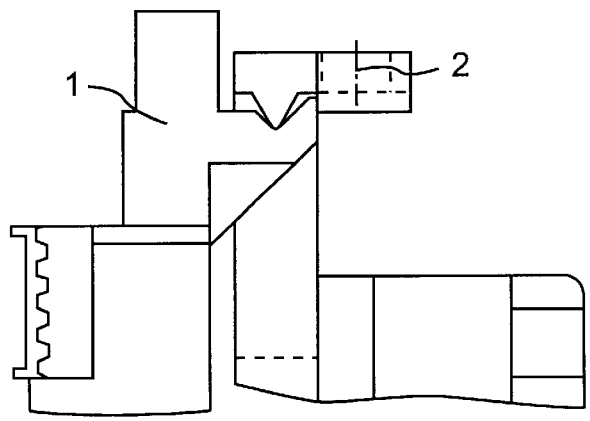
FIG. 2 is a left side view of the mutual engagement of holder 1 and oscillating arm 2 according to the present invention.

FIG. 2 shows a knife edge of the oscillating arm 2 in a prism bearing of the holder 1.

Figure 3:
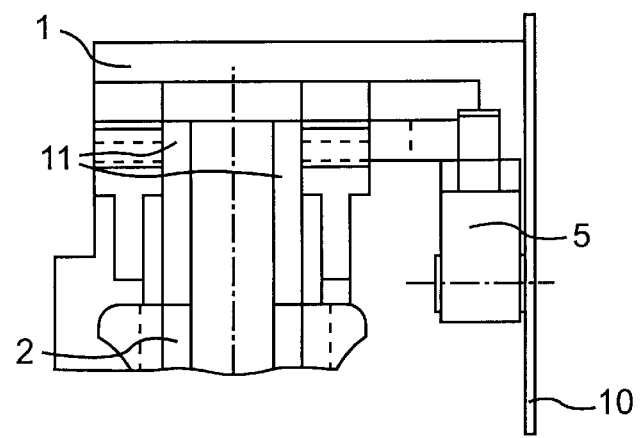
FIG. 3 is a front view of the holder 1 with the oscillating arm 2 of the present invention.

From FIG. 3 it will be seen that the oscillating arm 2 is mounted upstream of the holder 1 and a sensor 5 is arranged on a plate 10 sensors and switches off the analyzer when the pipette needle strikes against a solid object.

Figure 4:
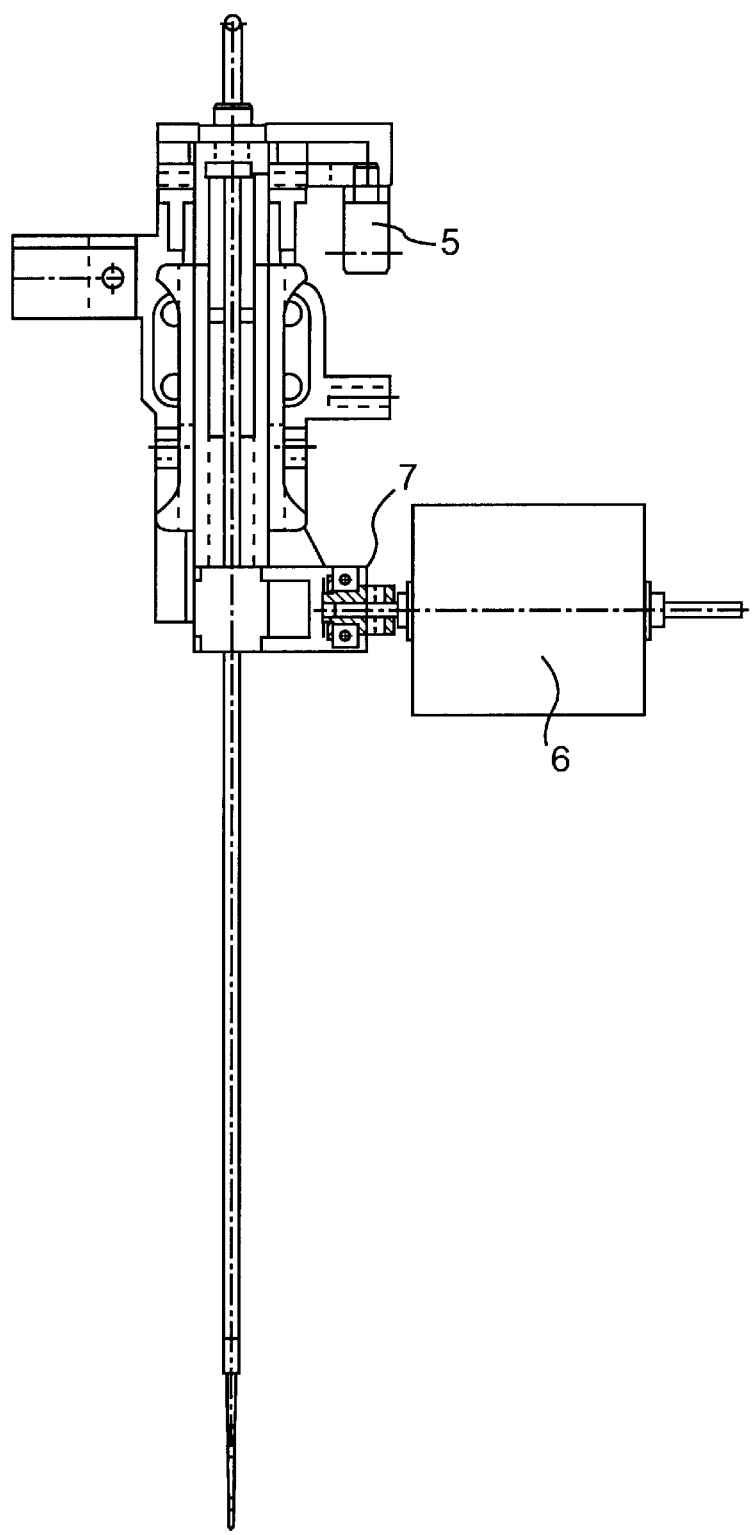
FIG. 4 is a front view of the exchangeable oscillating pipette needle according to the present invention, with an eccentric motor attached.

FIG. 4 shows a front view of the exchangeable oscillating pipette needle illustrating a drive motor with an eccentrically rotating shaft 6 and a drive fork 7 in which the eccentric shaft 6 is engaged for the purpose of generating oscillations.

Figure 5:
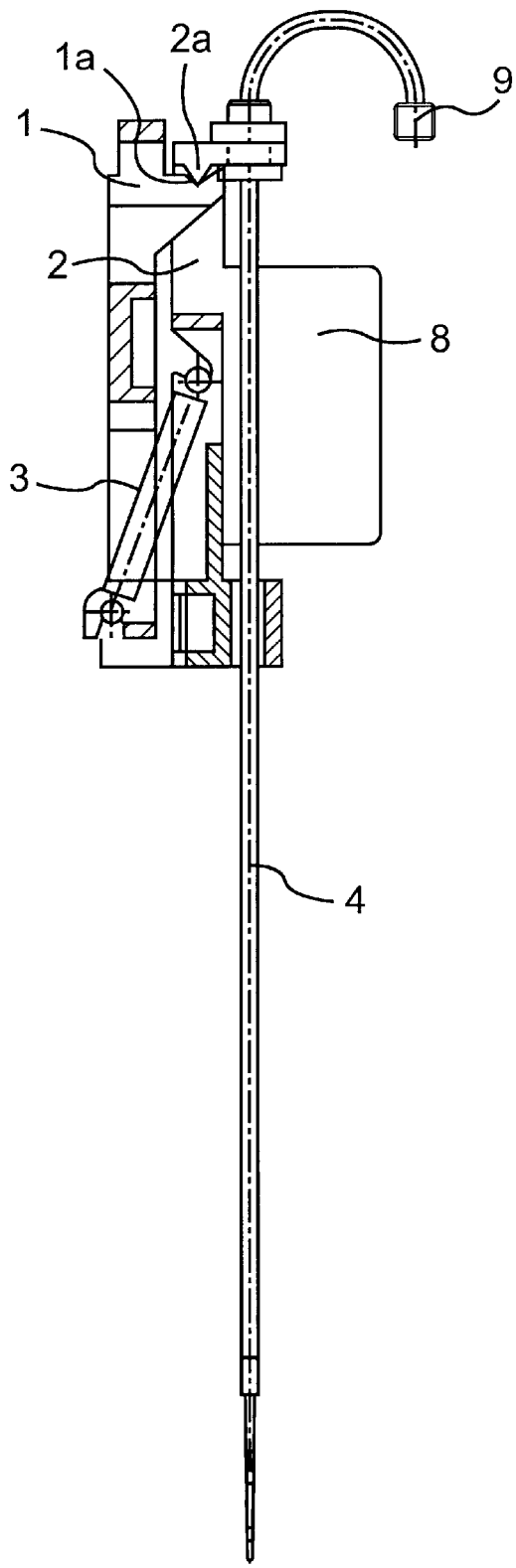
FIG. 5 is a side view of the exchangeable oscillating pipette needle according to the present invention.
Figure 6:
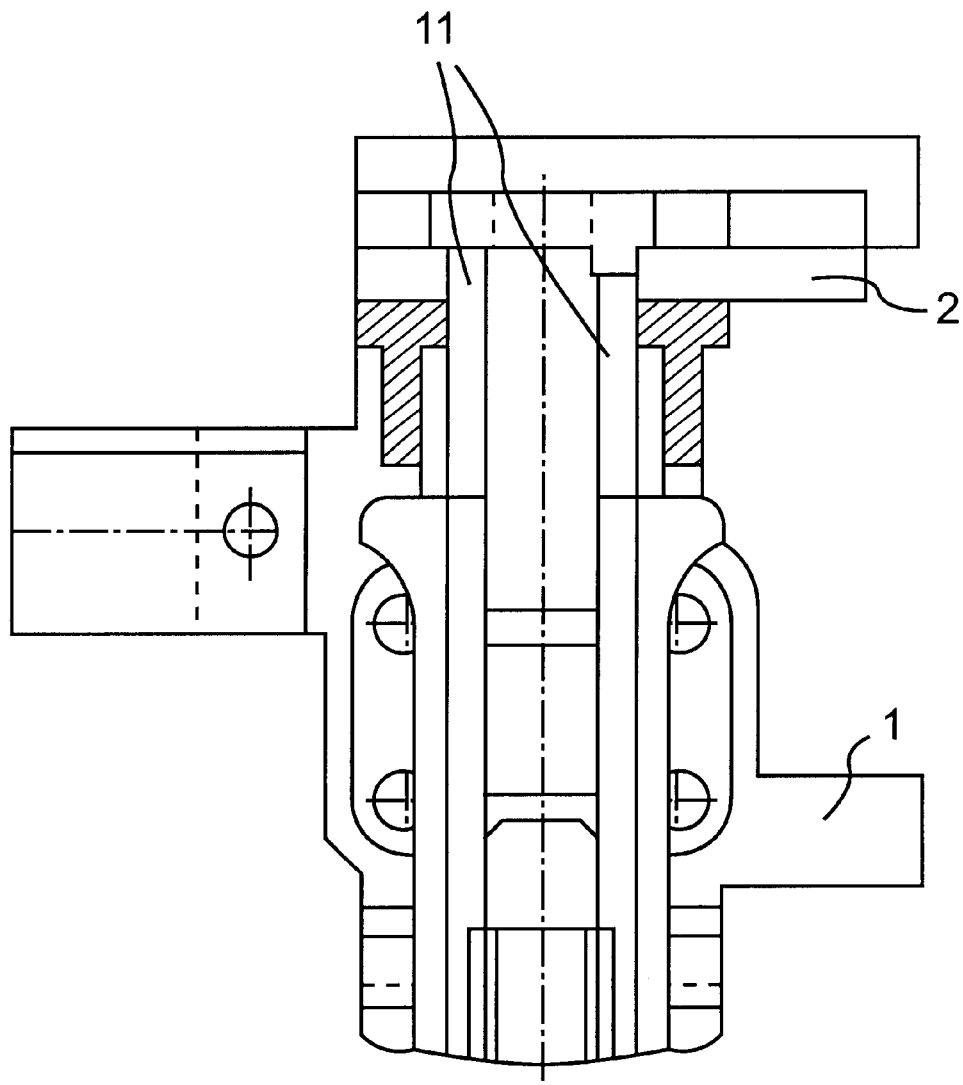
FIG. 6 is a front view of the oscillating pipette needle, of the present invention with a section of the prism.

FIG. 5 shows a side view of the exchangeable oscillating pipette needle with the holder 1, the oscillating arm 2, a tension spring 3, the pipette needle 4, grips 8 for exchanging the pipette needle, and a connection piece 9 provided for the admission of reagents.

These figures show that the exchangeable oscillating pipette needle comprises of two subsidiary groups, namely the oscillating arm 2 with the pipette needle 4, and a rigidly secured holder 1. A tension spring 3, connected to the holder 1 in a non-releasable manner, can engage in an insert opening of ribs 11 of the oscillating arm 2 and can thus press the oscillating arm 2 against the holder 1. In this way, a restoring force acts on the oscillating arm 2 and ensures that it does not leave its defined position during oscillation.

To avoid damaging the pipette needle 4, it is of the utmost importance that the needle 4 retains its predetermined positions during the entire analyzing process and that collisions with solid parts of the analyzer or of the measurement cell are avoided. According to the present invention, and as shown in FIG. 5, this is ensured by secure and reproducible positioning of the oscillating arm 2 by means of a prism 2a of the arm 2 resting on a knife edge bearing 1a of the holder and being secured on ribs 11 which ensure lateral fixing of the oscillating arm 2.

Although the main object of the present invention is to make it possible to replace a damaged oscillating pipette needle 4 in a simple way, the need for such replacement should of course be reduced by the fact that damage to the pipette needle 4 is largely eliminated. This is made possible by the flexible mounting, afforded by the tension spring 3, of the oscillating arm 2, which permits a vertical movement of the oscillating arm 2. If the pipette needle 4 strikes against a solid object, then the neddle 4 slides out of the prism mounting of the holder 1 and, moves upward in so doing it interrupts the current flow by triggering the sensor 5. The analyzer is in this way immediately switched off and destruction of the pipette needle 4 is avoided. However, if replacement of the pipette needle 4 is required, then the oscillating arm 2 can be pushed upward from the knife-edge bearing, released from the tension spring 3 and removed in a single maneuver. To do this, the grip 8 need simply be held with two fingers and pushed upward.

When using the oscillating pipette needle according to the present invention, it is advantageous for the needle to be heated. The oscillations needed for thoroughly mixing the reagents with the body fluid to be examined are generated by an eccentric motor equipped with an eccentrically rotating shaft 6, or alternatively by an eccentrically mounted roller.

Whereas the oscillating pipette needles used to date are incorporated rigidly and in a fixed manner in the analyzer, according to the present invention this applies only to the mounting of the oscillating arm. Thus, according to the present invention, it is no longer necessary to unscrew the entire pipette system and change it completely. It is now enough to replace only the oscillating arm carrying the pipette needle 4. This is such a simple procedure that the personnel operating the analyzer can perform this repair by means of a single maneuver in which the damaged oscillating pipette needle 4 is exchanged for a corresponding replacement part. Thus, according to the present invention, a solution is provided which permits rapid and inexpensive repair of a damaged oscillating pipette needle.

LIST OF REFERENCE SYMBOLS

1 Holder
2 Oscillating arm
3 Tension spring
4 heatable pipette needle
5 Sensor
6 Drive motor with eccentric
7 Drive fork for eccentric
8 Grip for exchanging
9 Admission for reagents
10 Plate
11 Ribs

We claim:

1. An oscillating pipette needle holder system for an automatic analyzer for examining biological body fluids, comprising a holder for the purpose of introducing a pipette needle into an analyzer and withdrawing it from the analyzer, the holder having a tension spring. an oscillating arm carrying the pipette needle and resting on a knife-edge bearing of the holder, the oscillating arm being fixed in a stationary position by the tension spring, and being releasably connected to the holder by the tension spring.

2. The oscillating pipette needle holder system of claim 1, wherein the knife-edge bearing is secured on ribs of the oscillating arm to ensure a lateral fixing of the oscillating arm.

3. The oscillating pipette needle holder system of claim 1, wherein the tension spring engages in an insert opening of ribs of the oscillating arm and can press the oscillating arm against the holder.

4. The oscillating pipette needle holder system of claim 1, wherein the pipette needle comprises a material capable of being heated.

5. The oscillating pipette needle holder system of claim 1, wherein the oscillating arm has a drive fork with an eccentric rotating shaft engagable with the drive fork for generating oscillations.

6. The oscillating pipette needle holder system of claim 1, wherein a connection piece for admission of reagents is provided on the oscillating arm.

7. The oscillating pipette needle holder system of claim 1, wherein the oscillating arm is movable in the vertical direction upon assembly, and further including a sensor arranged on a plate to switch the analyzer off upon vertical movement of the oscillating arm.

8. The oscillating pipette needle holder system of claim 1 wherein the oscillating arm has grips for exchanging the pipette needle.

9. An oscillating pipette needle holder system for an automatic analyzer for examining biological body fluids, comprising:
 a flexibly mounted oscillating arm;
 a pipette needle held by said oscillating arm; and
 a holder releasably connected to the flexibly mounted oscillating arm for stabilizing said arm.

10. The oscillating pipette needle holder system of claim 9, wherein the oscillating arm is releasably connected to the holder by a tension spring.

11. The oscillating pipette needle holder system of claim 9, wherein the oscillating arm is vertically moveable to permit replacement of the pipette needle.

12. The oscillating pipette needle holder system of claim 9, further including a knife-edge bearing upon which said oscillating arm rests.

13. The oscillating pipette needle holder system of claim 9, wherein the oscillating arm is releasably connected to the holder by a tension spring which can press the oscillating arm against the holder for stabilization.

* * * * *